United States Patent [19]

Hoek et al.

[11] Patent Number: Plant 5,815

[45] Date of Patent: Dec. 2, 1986

[54] CHRYSANTHEMUM PLANT NAMED DELTA

[75] Inventors: Leendert A. Hoek; Jan Hoek, both of The Hague, Netherlands

[73] Assignee: Hoek Breeding B.V., Netherlands

[21] Appl. No.: 678,042

[22] Filed: Dec. 4, 1984

[51] Int. Cl.[4] ..... A01H 5/00

[52] U.S. Cl. ..... Plt./74

[58] Field of Search ..... Plt./74

*Primary Examiner*—R. E. Bagwill

*Attorney, Agent, or Firm*—Schwartz, Jeffery, Schwaab, Mack, Blumenthal & Evans

[57] ABSTRACT

A new and distinct cultivar of Chrysanthemum named Delta and particularly characterized by its flat capitulum form and daisy capitulum type, pink ray floret color devoid of discoloration, diameter across face of capitulum ranging from 70 to 85 mm. at maturity, uniform nine weeks response, upright branching pattern and minimum pollen production.

1 Drawing Figure

The present invention comprises a new and distinct cultivar of *Chrysanthemum morifolium,* Ramat., hereinafter referred to by the cultivar name Delta.

Delta is a product of a planned breeding program which had the objective of creating new Chrysanthemum cultivars with nine (9) weeks flowering response, and with the ability to produce all year round the same level of quality, similar to the Horim family of cultivars.

Delta was originated from a hybridization made by the present inventors in a controlled breeding program in 's-Gravenhage, the Netherlands in 1979. The female parent was No. 65c-76 (unnamed seedling), a deep pink daisy. The male parent of Delta was Horim, a white daisy with four (4) rows of petals. Delta was discovered and selected as one flowering plant within the progeny of the stated parentage by Leendert A. Hoek on Nov. 5, 1980 in a controlled environment in 's-Gravenhage, the Netherlands.

The first act of asexual reproduction of Delta was accomplished when vegetative cuttings were taken from the initial selection on Jan. 12, 1981 in a controlled environment in 's-Gravenhage, the Netherlands by a technician working under formulations established and supervised by Leendert A. Hoek. Horticultural examination of selected units initiated July 20, 1981 has demonstrated that the combination of characteristics as herein disclosed for Delta are firmly fixed and are retained through successive generations of asexual reproduction.

Delta has not been observed under all possible environmental conditions. The phenotype may vary significantly with variations in environment such as temperature, light intensity and day length. The following observations, measurements and comparisons describe plants grown in 's-Gravenhage, the Netherlands under greenhouse conditions which approximate those generally used in commercial practice.

The following traits have been repeatedly observed and are determined to be basic characteristics of Delta, which in combination distinguish this Chrysanthemum as a new and distinct cultivar:

1. Flat capitulum form.
2. Daisy capitulum type.
3. Pink ray floret color, with excellent color retention.
4. Green (immature) to yellow (mature) disc floret color.

5. Diameter across face of capitulum ranging from 70 to 85 mm. at maturity.
6. Uniform nine weeks photoperiodic flowering response to short days.
7. Medium to large plant height (requiring 3–4 weeks prior to short days).
8. Upright branching pattern.
9. Minimum pollen production.

Of the many commercial cultivars known to the present inventors, the most similar in comparison to Delta is Dark Miros, a 10 week deep pink daisy type cultivar well known in Europe. Reference is made to attached Chart A which compares certain characteristics of Delta to those same characteristics of Dark Miros. In general comparison to Dark Miros, Delta has a slightly deeper pink color; has better color retention under high finishing temperatures; produces less pollen; has a larger capitulum size, and has a one week earlier response. The capitulum form, type and plant height of Delta are similar to those same characteristics of Dark Miros.

The accompanying photographic drawing shows typical inflorescence and foliage characteristics of Delta, with colors being as nearly true as possible with illustrations of this type.

In the following description color references are made to The Royal Horticultural Society Colour Chart. The color values were determined between noon and 2:00 P.M. on Jan. 13, 1981 under natural light conditions of 30 foot candle light intensity at 's-Gravenhage, the Netherlands.

Classification:

*Botanical.*—*Chrysanthemum morifolium,* Ramat., cv Delta.

*Commercial.*—Cut daisy spray.

I. INFLORESCENCE

A. Capitulum:

*Form.*—Generally flat.

*Type.*—Daisy.

*Diameter across face.*—70 mm.

B. Corolla of ray florets:

*Color (general tonality from a distance of three meters).*—Pink.

*Color (upper surface).*—R.H.S. 68C, excellent color retention.

C. Corolla of disc florets:

*Color* (*mature*).Yellow, R.H.S. 3A.

*Color* (*immature*).—Green, R.H.S. 154A.

II PLANT

A. General appearance:

*Height.*—Medium to large for this type of cultivar.

B. Foliage:

*Color* (*upper surface*).—137A.

*Shape.*—Medium sized, elongated, with moderate lobes and serration along both edges of leaf.

CHART A

COMPARISON OF DELTA AND DARK MIROS

| CULTIVAR | RAY FLORET COLOR | CAPITULUM FORM AND TYPE | POLLEN PRODUCTION |
|---|---|---|---|
| DELTA | deep pink RHS 68C | flat daisy | sparse |

CHART A-continued

COMPARISON OF DELTA AND DARK MIROS

| | | | |
|---|---|---|---|
| DARK MIROS | deep pink RHS 68D | flat daisy | abundant |

| CULTIVAR | DIAMETER ACR ACROSS FACE OF CAPITULUM | PLANT HEIGHT | FLOWERING RESPONSE PERIOD |
|---|---|---|---|
| DELTA | 70 to 99 mm. | medium | 9 week |
| DARK MIROS | 60 to 75 mm. | medium | 10 week |

We claim:

1. A new and distinct cultivar of Chrysanthemum named Delta, as described and illustrated, and particularly characterized by its flat capitulum form and daisy capitulum type, pink ray floret color devoid of discoloration, diameter across face of capitulum ranging from 70 to 85 mm. at maturity, uniform nine weeks response, upright branching pattern and minimum pollen production.

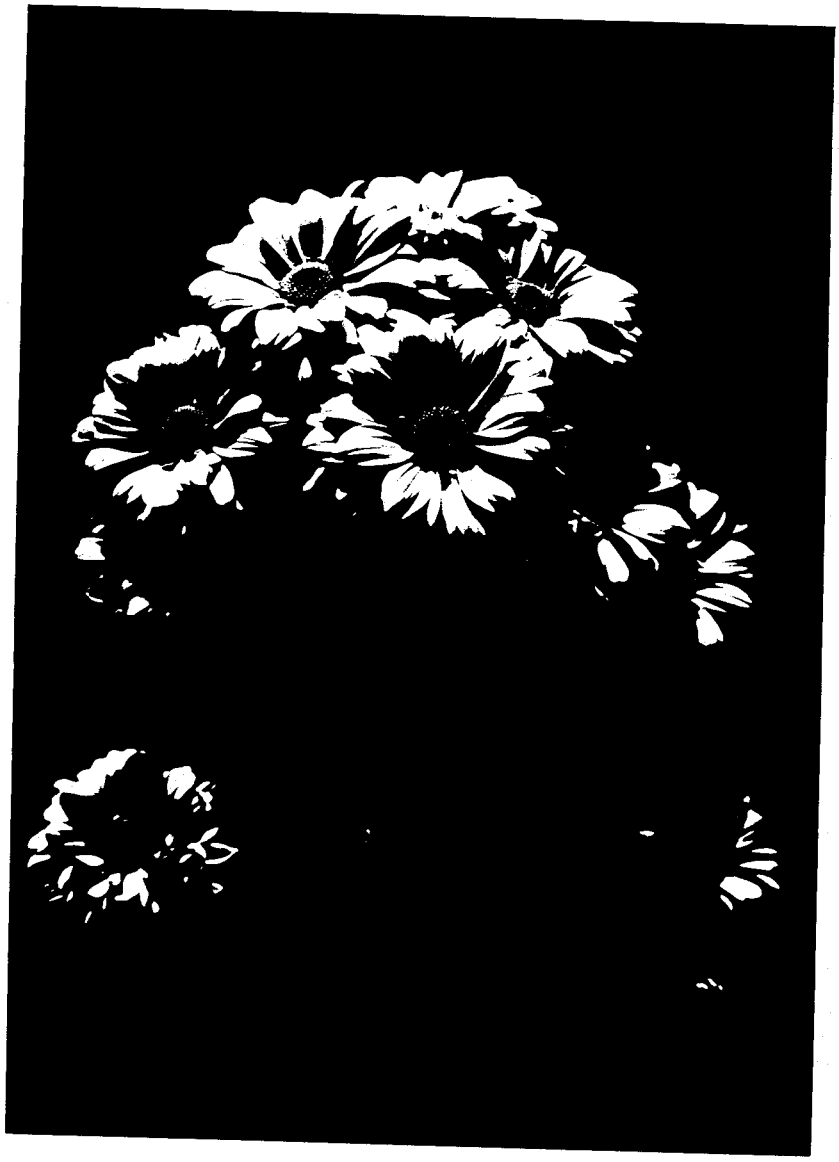

* * * * *